(12) United States Patent
Bown et al.

(10) Patent No.: US 10,967,153 B2
(45) Date of Patent: *Apr. 6, 2021

(54) SHAPE MEMORY MEDICAL DEVICE AND METHODS OF USE

(71) Applicant: C. R. Bard, Inc., Murray Hill, NJ (US)

(72) Inventors: Matthew W. Bown, West Bountiful, UT (US); David M. Butts, Riverton, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 379 days.

This patent is subject to a terminal disclaimer.

(21) Appl. No.: 14/309,782

(22) Filed: Jun. 19, 2014

(65) Prior Publication Data
US 2014/0303600 A1 Oct. 9, 2014

Related U.S. Application Data

(62) Division of application No. 12/028,555, filed on Feb. 8, 2008, now Pat. No. 8,758,268.

(60) Provisional application No. 60/900,202, filed on Feb. 8, 2007.

(51) Int. Cl.
A61M 25/09 (2006.01)
(52) U.S. Cl.
CPC ... A61M 25/09 (2013.01); A61M 2025/09108 (2013.01); A61M 2025/09125 (2013.01); A61M 2025/09133 (2013.01); A61M 2025/09141 (2013.01); Y10T 29/49 (2015.01)

(58) Field of Classification Search
CPC .......................................... A61M 2025/09141
See application file for complete search history.

(56) References Cited

U.S. PATENT DOCUMENTS

| 3,827,426 A | 8/1974 | Page et al. |
| 4,283,233 A | 8/1981 | Goldstein et al. |
| 4,335,571 A | 6/1982 | Tarantola |
| 4,352,542 A | 10/1982 | Tydings |
| 4,380,433 A | 4/1983 | Ellman et al. |

(Continued)

FOREIGN PATENT DOCUMENTS

| CN | 102427844 A | 4/2012 |
| EP | 0515201 A1 | 11/1992 |

(Continued)

OTHER PUBLICATIONS

"malleable", www.merriam-webster.com/dictionary/malleable, printed on Nov. 21, 2017, 13 pages.*

(Continued)

Primary Examiner — Matthew Kremer
(74) Attorney, Agent, or Firm — Rutan & Tucker LLP

(57) ABSTRACT

A method of treating a patient includes providing a guidewire having an elongate body defining a proximal end and a distal end, the elongate body including a shapeable portion disposed proximate the proximal end, the shapeable portion being malleable so as to be shaped into a shape and remain in the shape until reshaped. The distal end of the elongate body is advanced into a vasculature of the patient. The shapeable portion of the elongate body is shaped into a first shape that prevents advancement of the guidewire further into the vasculature of the patient.

7 Claims, 6 Drawing Sheets

(56) References Cited

U.S. PATENT DOCUMENTS

| | | | |
|---|---|---|---|
| 4,425,908 A | 1/1984 | Simon | |
| 4,484,955 A | 11/1984 | Hochstein | |
| 4,650,472 A | 3/1987 | Bates | |
| 4,665,906 A | 5/1987 | Jervis | |
| 4,860,757 A | 8/1989 | Lynch et al. | |
| 4,917,094 A | 4/1990 | Lynch et al. | |
| 4,925,445 A | 5/1990 | Sakamoto et al. | |
| 4,934,380 A | 6/1990 | de Toledo | |
| 4,957,117 A | 9/1990 | Wysham | |
| 5,060,660 A | 10/1991 | Gambale et al. | |
| 5,069,226 A | 12/1991 | Yamauchi et al. | |
| 5,090,958 A | 2/1992 | Sahota | |
| 5,125,906 A | 6/1992 | Fleck | |
| 5,171,383 A | 12/1992 | Sagae et al. | |
| 5,186,179 A | 2/1993 | MacEachern | |
| 5,211,183 A * | 5/1993 | Wilson | A61M 25/0158 600/434 |
| 5,238,004 A * | 8/1993 | Sahatjian | A61M 25/0015 600/434 |
| 5,243,996 A | 9/1993 | Hall | |
| 5,273,042 A | 12/1993 | Lynch et al. | |
| 5,281,203 A | 1/1994 | Ressemann | |
| 5,299,580 A | 4/1994 | Atkinson et al. | |
| 5,341,818 A | 8/1994 | Abrams et al. | |
| 5,365,943 A | 11/1994 | Jansen | |
| 5,366,444 A | 11/1994 | Martin | |
| 5,368,049 A | 11/1994 | Raman et al. | |
| 5,383,467 A | 1/1995 | Auer et al. | |
| 5,437,288 A | 8/1995 | Schwartz et al. | |
| 5,438,993 A | 8/1995 | Lynch et al. | |
| 5,448,993 A | 9/1995 | Lynch et al. | |
| 5,452,726 A | 9/1995 | Burmeister et al. | |
| 5,643,281 A | 7/1997 | Suhocki et al. | |
| 5,656,029 A | 8/1997 | Imran et al. | |
| 5,690,120 A | 11/1997 | Jacobsen et al. | |
| 5,810,012 A | 9/1998 | Lynch et al. | |
| 5,827,241 A * | 10/1998 | Douk | A61M 25/0113 600/434 |
| 5,830,156 A | 11/1998 | Ali | |
| 5,843,050 A | 12/1998 | Jones et al. | |
| 5,865,721 A | 2/1999 | Andrews et al. | |
| 5,876,356 A | 3/1999 | Viera et al. | |
| 5,935,108 A | 8/1999 | Katoh et al. | |
| 6,004,279 A | 12/1999 | Crowley et al. | |
| 6,011,988 A | 1/2000 | Lynch et al. | |
| RE36,628 E | 3/2000 | Sagae et al. | |
| 6,106,642 A | 8/2000 | DiCarlo et al. | |
| 6,238,404 B1 | 5/2001 | Hidalgo et al. | |
| 6,240,727 B1 | 6/2001 | Goldstein et al. | |
| 6,254,550 B1 * | 7/2001 | McNamara | A61M 25/09 600/585 |
| 6,277,100 B1 | 8/2001 | Raulerson et al. | |
| 6,352,515 B1 | 3/2002 | Anderson et al. | |
| 6,355,016 B1 | 3/2002 | Bagaoisan et al. | |
| 6,425,887 B1 | 7/2002 | McGuckin et al. | |
| 6,440,088 B1 | 8/2002 | Jacobsen et al. | |
| 6,464,650 B2 | 10/2002 | Jafari et al. | |
| 6,477,402 B1 | 11/2002 | Lynch et al. | |
| 6,517,481 B2 | 2/2003 | Hoek et al. | |
| 6,551,281 B1 | 4/2003 | Raulerson et al. | |
| 6,572,608 B1 | 6/2003 | Lee et al. | |
| 6,592,559 B1 | 7/2003 | Pakter et al. | |
| 6,592,570 B2 | 7/2003 | Abrams et al. | |
| 6,669,670 B1 | 12/2003 | Muni et al. | |
| 6,673,025 B1 | 1/2004 | Richardson et al. | |
| 6,682,493 B2 | 1/2004 | Mirigian | |
| 6,761,696 B1 | 7/2004 | Wong | |
| 6,939,361 B1 | 9/2005 | Kleshinski | |
| 7,237,313 B2 | 7/2007 | Skujins et al. | |
| 7,670,302 B2 | 3/2010 | Griffin et al. | |
| 8,758,268 B2 * | 6/2014 | Bown | A61M 25/09 148/563 |
| 2002/0062092 A1 | 5/2002 | Muni et al. | |
| 2003/0069522 A1 | 4/2003 | Jacobsen et al. | |
| 2003/0114777 A1 | 6/2003 | Griffin et al. | |
| 2003/0216668 A1 | 11/2003 | Howland et al. | |
| 2004/0093017 A1 | 5/2004 | Chanduszko | |
| 2004/0122416 A1 | 6/2004 | Schweikert et al. | |
| 2004/0129352 A1 | 7/2004 | Shiota | |
| 2004/0168752 A1 | 9/2004 | Julien | |
| 2004/0181174 A2 | 9/2004 | Davis et al. | |
| 2004/0199088 A1 | 10/2004 | Bakos et al. | |
| 2004/0243095 A1 | 12/2004 | Nimkar et al. | |
| 2005/0054950 A1 | 3/2005 | Parins | |
| 2005/0054953 A1 * | 3/2005 | Ryan | A61M 25/09 600/585 |
| 2005/0145307 A1 | 7/2005 | Shireman et al. | |
| 2006/0047223 A1 | 3/2006 | Grandfield et al. | |
| 2006/0106407 A1 | 5/2006 | McGuckin et al. | |
| 2006/0157060 A1 | 7/2006 | Nelson | |
| 2006/0264834 A1 | 11/2006 | Vaillancourt | |
| 2007/0032746 A1 | 2/2007 | Sell | |
| 2007/0073387 A1 | 3/2007 | Forster et al. | |
| 2007/0088254 A1 | 4/2007 | DeStefano | |
| 2007/0100285 A1 | 5/2007 | Griffin et al. | |
| 2007/0112282 A1 | 5/2007 | Skujins et al. | |
| 2007/0123805 A1 | 5/2007 | Shireman et al. | |
| 2007/0213689 A1 | 9/2007 | Grewe et al. | |
| 2007/0244413 A1 | 10/2007 | Biggins | |
| 2007/0244550 A1 | 10/2007 | Eidenschink | |
| 2008/0064988 A1 | 3/2008 | Carter et al. | |
| 2008/0194994 A1 | 8/2008 | Bown et al. | |
| 2010/0249655 A1 | 9/2010 | Lemon | |
| 2011/0257592 A1 | 10/2011 | Ventura et al. | |
| 2014/0094778 A1 | 4/2014 | Bown et al. | |

FOREIGN PATENT DOCUMENTS

| | | |
|---|---|---|
| EP | 0739641 A1 | 10/1996 |
| EP | 860177 A2 | 8/1998 |
| EP | 0868924 A2 | 10/1998 |
| EP | 2414020 | 2/2012 |
| IN | 7626/DELNP/2011 | 2/2013 |
| JP | 1049571 A | 2/1989 |
| JP | S64-49571 A | 2/1989 |
| JP | 2005342470 A | 12/2005 |
| WO | 1995019800 A2 | 7/1995 |
| WO | 2000069359 A1 | 11/2000 |
| WO | 2007079014 A2 | 7/2007 |
| WO | 2007121131 A2 | 10/2007 |
| WO | 2008024597 A2 | 2/2008 |
| WO | 2010114800 A1 | 10/2010 |

OTHER PUBLICATIONS

"Shape." Merriam-Webster.com Dictionary, Merriam-Webster, https://www.merriam-webster.com/dictionary/shape. Accessed May 26, 2020. (Year: 2020).*

"Malleable." Merriam-Webster.com Dictionary, Merriam-Webster, https://www.merriamwebster.com/dictionary/malleable. Accessed May 26, 2020. (Year: 2020).*

CN201310583330.3 filed Nov. 20, 2013, Second Office Action dated Feb. 26, 2016.

JP 2013-125780 filed Jun. 14, 2013 Office Action dated May 27, 2014.

U.S. Appl. No. 12/749,359, filed Mar. 29, 2010 Final Office Action dated Sep. 26, 2014.

U.S. Appl. No. 12/749,359, filed Mar. 29, 2010 Non-Final Office Action dated Jun. 19, 2014.

U.S. Appl. No. 14/098,147, filed Dec. 5, 2013 Non-Final Office Action dated Jun. 3, 2016.

CN 20080004398.9 filed Feb. 8, 2008 First Office Action dated Dec. 23, 2011.

CN 20080004398.9 filed Feb. 8, 2008 Second Office Action dated Oct. 8, 2012.

CN 20088004398.9 filed Feb. 8, 2008 Third Office Action dated Apr. 27, 2013.

CN 201080021838.9 filed Nov. 18, 2011 First Office Action dated Feb. 20, 2013.

(56) References Cited

OTHER PUBLICATIONS

CN 201080021838.9 filed Nov. 18, 2011 Second Office Action dated Sep. 30, 2013.
EP 10759267.7 filed Sep. 29, 2011 Supplemental European Search Report dated Aug. 1, 2013.
JP 2009-549266 filed Feb. 8, 2008 Interrogatory dated Sep. 3, 2013.
JP 2009-549266 filed Feb. 8, 2008 Office Action dated Apr. 10, 2012.
JP 2009-549266 filed Feb. 8, 2008 Office Action dated Feb. 14, 2013.
PCT/US2008/053460 filed Feb. 8, 2008 International Preliminary Report on Patentability dated Aug. 11, 2009.
PCT/US2008/053460 filed Feb. 8, 2008 Search Report dated Sep. 16, 2008.
PCT/US2008/053460 filed Feb. 8, 2008 Written Opinion dated Sep. 16, 2008.
PCT/US2010/029089 filed Mar. 29, 2010 Search Report dated May 20, 2010.
PCT/US2010/029089 filed Mar. 29, 2010 Written Opinion dated May 20, 2010.
U.S. Appl. No. 12/028,555, filed Feb. 8, 2008 Advisory Action dated Feb. 16, 2012.
U.S. Appl. No. 12/028,555, filed Feb. 8, 2008 Final Office Action dated Dec. 7, 2011.
U.S. Appl. No. 12/028,555, filed Feb. 8, 2008 Final Office Action dated May 21, 2013.
U.S. Appl. No. 12/028,555, filed Feb. 8, 2008 Non-Final Office Action dated Apr. 20, 2012.
U.S. Appl. No. 12/028,555, filed Feb. 8, 2008 Non-Final Office Action dated Dec. 11, 2012.
U.S. Appl. No. 12/028,555, filed Feb. 8, 2008 Non-Final Office Action dated Dec. 29, 2010.
U.S. Appl. No. 12/028,555, filed Feb. 8, 2008 Non-Final Office Action dated Jun. 17, 2011.
U.S. Appl. No. 12/028,555, filed Feb. 8, 2008 Non-Final Office Action dated Sep. 13, 2012.
U.S. Appl. No. 12/028,555, filed Feb. 8, 2008 Notice of Allowance dated Feb. 19, 2014.
U.S. Appl. No. 12/749,359, filed Mar. 29, 2010 Final Office Action dated Jul. 12, 2013.
U.S. Appl. No. 12/749,359, filed Mar. 29, 2010 Non-Final Office Action dated Dec. 24, 2012.
CN201310583330.3 filed Nov. 20, 2013, First Office Action dated Jun. 15, 2015.
U.S. Appl. No. 14/098,147, filed Dec. 5, 2013 Advisory Action dated Feb. 6, 2017.
U.S. Appl. No. 14/098,147, filed Dec. 5, 2013 Final Office Action dated Nov. 23, 2016.
U.S. Appl. No. 14/098,147, filed Dec. 5, 2013 Board Decision dated Feb. 28, 2019.

* cited by examiner

SHAPE MEMORY MEDICAL DEVICE AND METHODS OF USE

CROSS-REFERENCE TO RELATED APPLICATION

This application is a division of U.S. patent application Ser. No. 12/028,555, filed Feb. 8, 2008, now U.S. Pat. No. 8,758,268, which claims the benefit of the U.S. Provisional Application No. 60/900,202, filed Feb. 8, 2007, each of which is incorporated herein by reference in its entirety.

TECHNOLOGY FIELD

The present invention generally relates to medical devices. In particular, embodiments of the present invention relate to a medical device, such as a guidewire, having a shaped proximal end to assist in the intravascular placement of various apparatus.

BRIEF SUMMARY

Guidewires are commonly employed to assist in placing medical apparatus intravascularly within a patient. One material commonly employed in forming guidewires is nitinol, an alloy containing both nickel and titanium. Nitinol is preferred for many guidewires because it offers excellent kink resistance, a quality that eases guidewire advancement into the patient vasculature.

It is generally advantageous to prevent a guidewire from advancing into the patient vasculature further than is desired. If not properly secured by a clinician during patient insertion, however, the guidewire may be inadvertently and undesirably pulled-by blood flow or other means-further into the vasculature. If the guidewire has been placed in its desired position prior to such inadvertent advancement, the clinician must then partially pull the guidewire out and position it anew, costing time and effort, and increasing the possibility of injury to the patient. A need therefore exists in the art to overcome these challenges.

The present invention has been developed in response to the above and other needs in the art. Briefly summarized, embodiments of the present invention are directed to a shaped guidewire for use in medical applications. The guidewire is shaped so as to prevent inadvertent advancement of the guidewire into the corpus of a patient during use.

In one embodiment, the guidewire includes an elongate body that defines proximal and distal ends. The guidewire body further defines a shaped portion that is positioned intermediate the proximal and distal ends. The shaped portion of the guidewire is at least partially composed of a shape memory material, such as nitinol, and is deflected from a longitudinal axis defined by an undeflected portion of the guidewire body.

The shaped portion is disposed in one embodiment at the proximal end of the guidewire so as to prevent the guidewire from undesirably advancing further into the vasculature of a patient during use. The shaped portion of the guidewire contacts the tissue or apparatus at the incision site of the patient, which causes the guidewire to cease further advancement. Various shaped configurations for the shaped portion are possible including semi-circular and geometric shapes.

In another embodiment, a proximal portion of the nitinol guidewire can be treated to impart malleability and enable deflection by a clinician. In this way, various devices such as needles, introducers, etc., can be fed over the proximal end of the guidewire before the shaped portion is formed. Methods for forming the shaped or malleable guidewire to include a deflected portion are also disclosed.

In yet another example embodiment, the guidewire can be composed of distinct materials according to guidewire region. For example, a proximal segment of the guidewire can include stainless steel while a distal segment includes nitinol. A guidewire so configured can be easily deflected and shaped at the proximal end due to its formation from stainless steel, while the nitinol distal segment retains desired kink-resistant qualities. The two segments can be joined together by welding or other suitable process.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-7 depict various features of embodiments of the present invention, which is generally directed to a guidewire for use in medical applications. The guidewire as disclosed herein includes a proximal portion that is deflected from the axis of the remainder of the guidewire so as to prevent inadvertent advancement of the guidewire into the corpus of a patient during use. In one embodiment, the guidewire is at least partially composed of a shape memory material, such as nitinol. Methods for forming the guidewire so as to include a deflected proximal portion are also disclosed.

Figure 1:
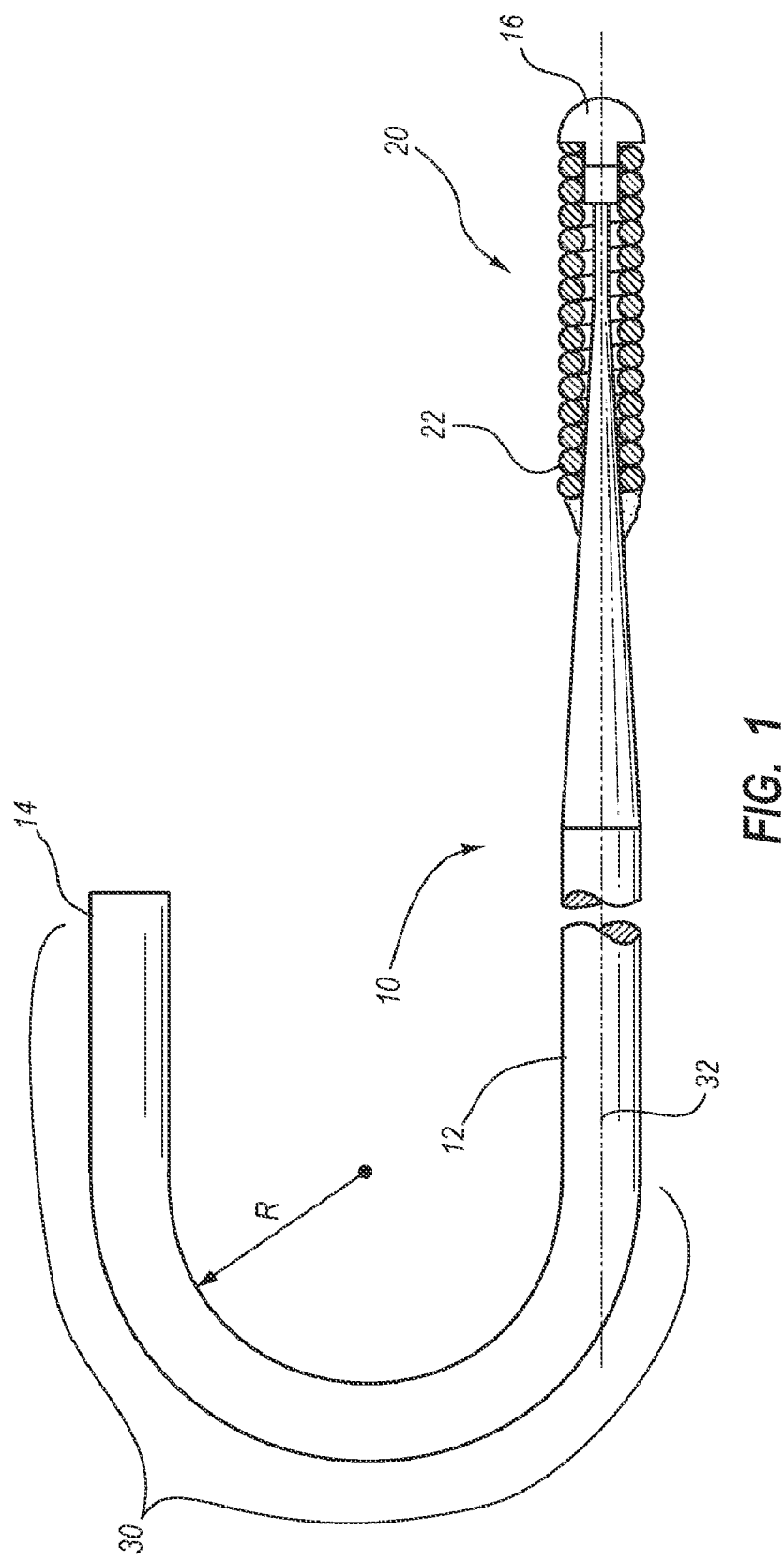
FIG. 1 is a side view of a guidewire configured in accordance with one example embodiment of the present invention.

Reference is first made to FIG. 1, which shows a guidewire, generally designated at 10, configured according to one example embodiment. As shown, the guidewire 10 includes an elongate body 12 defining both a proximal end 14 and a distal end 16. In this embodiment, a tip portion 20 is included near the distal end 16 and includes a coil 22 wrapped about the body 12. The coil 22 assists in providing atraumatic advancement of the guidewire 10 through the vasculature of a patient, via a percutaneous slit. Note that, once disposed in a vessel of the patient, the coil 22 of the tip portion 20 can obstruct the flow of fluids, such as blood, circulating in the vessel. As such, the interaction of the fluid with coil 22 can impart a distally directed force on the guidewire 10, tending to undesirably advance the tip portion 20 deeper into the vasculature. Embodiments of the present invention are intended to prevent such an occurrence. Note that in other embodiments the tip portion at the guidewire body distal end can include other configurations, such as a "J"-tip that facilitates advancement of the guidewire through tortuous paths in the patient vasculature without piercing the vessel wall.

In accordance with the present embodiment, the guidewire further includes a shaped proximal portion ("shaped portion"), generally designated at 30. As shown, the shaped portion 30 is located proximate the proximal end 14 of the guidewire 10. The shaped portion 30 is configured so as to prevent unintended advancement of the guidewire 10 into the vasculature of the patient during use. In the illustrated embodiment, the shaped portion 30 is shown deflected from a longitudinal axis 32 in a semi-circular bend having a radius R. As shown and discussed below, however, the shaped portion can have one of a variety of shapes.

Figure 2:
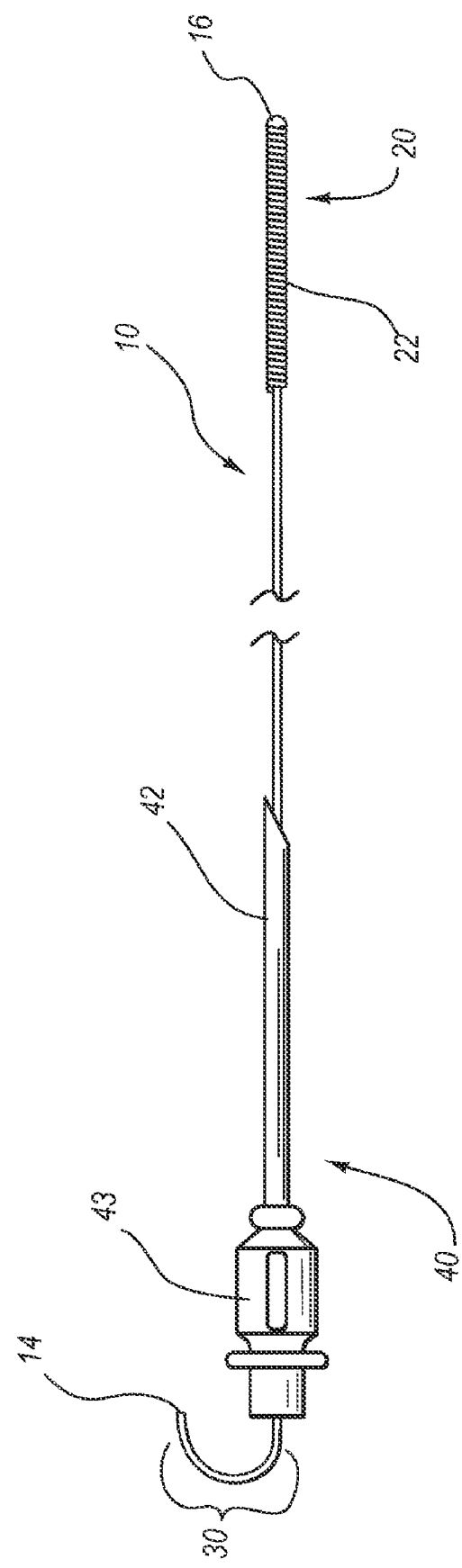
FIG. 2 is a side view showing the guidewire of FIG. 1 received through a needle assembly.

Together with FIG. 1, reference is now made to FIG. 2, which shows the guidewire 10 received in operable engagement with a needle assembly 40. Such a needle assembly 40 may be used in one embodiment to introduce the guidewire 10 into the vasculature of a patient. As shown, the guidewire 10 passes through both a needle 42 of the needle assembly 40 and a luer fitting 43 attached thereto. The shaped portion 30 of the guidewire 10, however, is sized and configured so as not to pass through the luer fitting 43, thereby preventing advancement of the guidewire 10 into the vasculature past a certain point. In other applications, the shaped portion will interact with a portion of another device, such as an introducer, or with the tissue of the patient proximate the incision, to inhibit further guidewire advancement.

Note that the shaped portion 30 of the guidewire 10 in one embodiment is somewhat flexible so as to enable medical devices, such as needles, introducers, and the like to be slid over the guidewire from the proximal end 14. Nonetheless, the shaped portion 30 is sufficiently stiff so as to return to its deflected state once any deforming load is removed therefrom.

In accordance with one embodiment, the shaped portion 30 of the guidewire 10 is composed of a shape memory material, including shape memory alloys, ferromagnetic shape memory materials, shape memory polymers, and the like. A "shape memory material" is understood herein to mean a material that can return to some previously defined shape after deformation, i.e., it "remembers" its geometry when subjected to an appropriate thermal procedure (a "one-way effect") or after a deforming load is removed therefrom, typically at higher ambient temperatures ("superelasticity").

One example of a shape memory material is nitinol, an alloy including, in one implementation, about 55-56% nickel and 44-45% titanium. In one embodiment, the shaped portion 30 includes nitinol. As mentioned above, nitinol can be employed as an excellent guidewire material for its kink-resistant properties. However, forming a bent or shaped portion in a nitinol guidewire has been difficult due to its shape memory properties. As will be disclosed, embodiments of the present invention contemplate forming such a bent portion, such as the shaped portion 30 shown in FIGS. 1 and 2, in a nitinol guidewire. Note that the shaped portion 30 may be composed entirely or partially of nitinol, or the entire guidewire 10 may include nitinol. Additionally, the relative concentrations of nickel and titanium in the nitinol material may vary from what is explicitly described herein.

In one embodiment the guidewire 10 has a diameter in the range of from about 0.018 to 0.038 inch and a length in a range of from about 35 to 180 centimeters, though other diameters and lengths are, of course, possible.

By way of example, shape memory materials can include alloys such as copper-zinc-aluminum alloys, copper-aluminum-nickel alloys, and nickel-titanium alloys. The shape memory properties of shape memory alloys are due to a temperature-dependent martensite phase transformation from a low-symmetry to a highly symmetric crystallographic structure. Those crystal structures are known as martensite and austenite. The temperatures at which a shape memory alloy changes its crystallographic structure are characteristic of the alloy and can be tuned by varying the elemental ratios. $A_s$ and $A_f$ are referred to as the temperatures at which the reverse transformation from martensite to austenite start and finish, respectively. By way of example, $A_s$ (austenite start), in some materials, varies between approximately $-150$ degrees Celsius to 200 degrees Celsius and $A_f$ (austenite finish) can range from changes in temperature from two to greater than 20 degrees Celsius.

Many shape memory alloys exhibit both shape memory and superelastic behavior. Alloy composition and the material's thermo-mechanical processing history dictate the temperatures where these properties exist. Superelasticity occurs when a shape memory alloy is mechanically deformed at a temperature above its $A_f$ temperature. This deformation causes a stress-induced phase transformation from austenite to martensite. The stress-induced martensite is unstable at temperatures above its $A_f$ so that when the stress is removed the material will immediately spring back or return to the austenite phase and its pre-stressed position. For reference, a graph 300, showing a phase transformation hysteresis curve 310, is included in FIG. 6.

In one embodiment, a guidewire having a proximal portion composed at least partially of nitinol can be processed by a "shape set annealing" process to define the shaped portion 30 as seen in FIGS. 1 and 2. To do so, the portion of the guidewire 10 proximate the proximal end 14 is deformed to a desired shape, then constrained to remain in the desired shape. This may be accomplished by a mandrel or other suitable device. The guidewire portion is then heat treated. Though actual temperatures and heating times vary according to the particular composition and characteristics of the portion being shaped, in one embodiment, the guidewire portion is heated to 500-550 degrees Celsius, followed by a rapid cooling, including for instance a water quench of the guidewire portion. In addition to maintaining the superelastic and shape memory properties, this process will impart to the guidewire portion a desired shape, such as the semi-circular configuration of the shaped portion 30 of the guidewire 10 shown in FIGS. 1 and 2.

Figure 4:
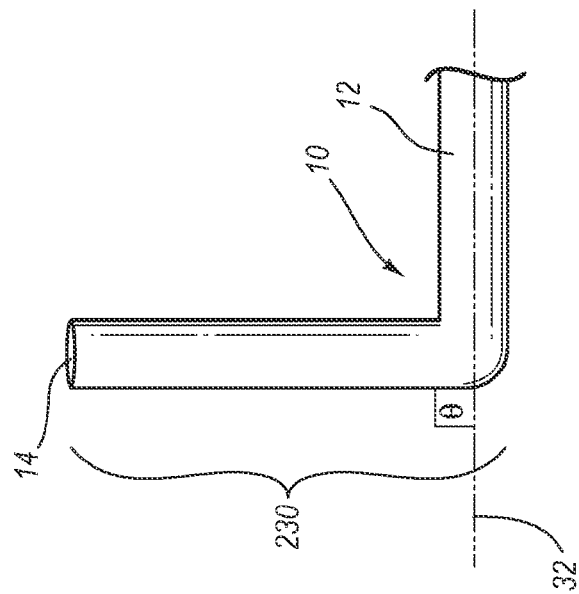
FIG. 4 is a side view showing a proximal portion of a guidewire configured according to yet another example embodiment.
Figure 3:
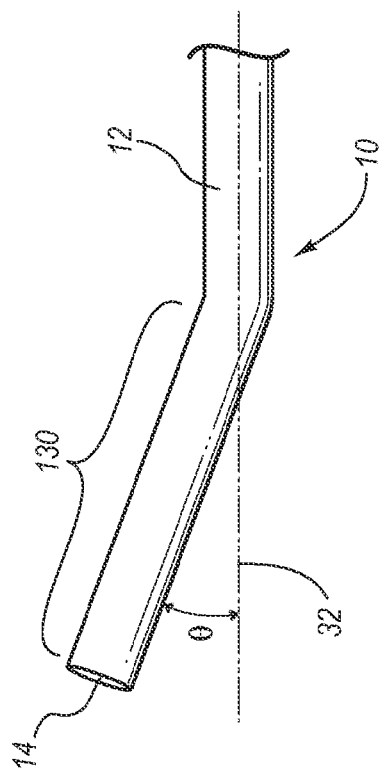
FIG. 3 is a side view showing a proximal portion of a guidewire configured according to another example embodiment.
Figure 5:
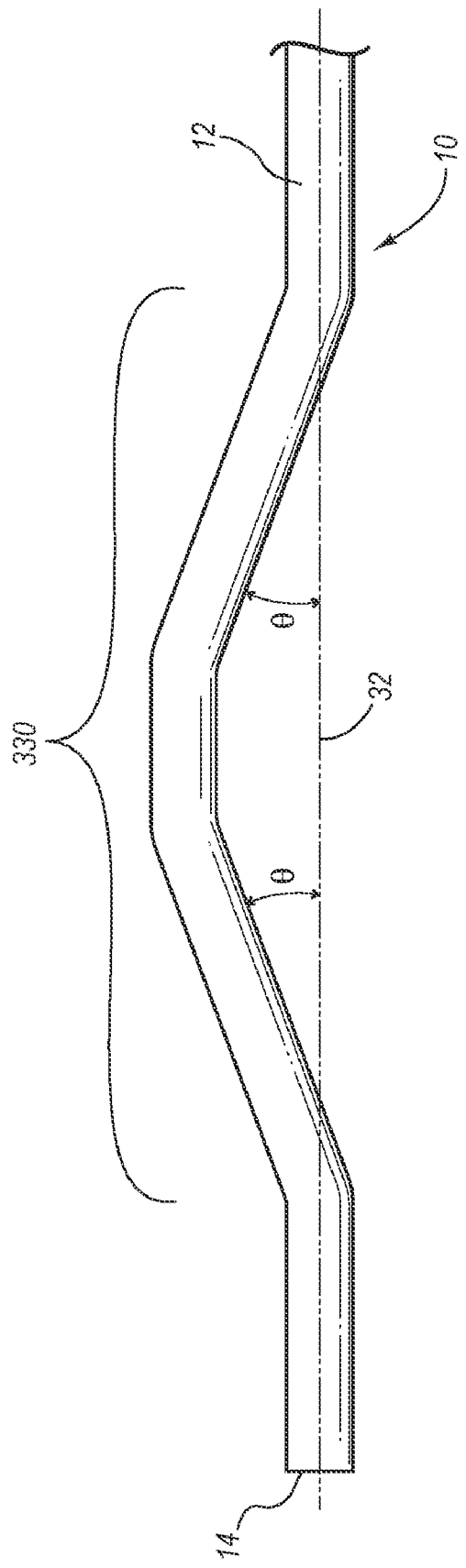
FIG. 5 is a side view showing a proximal portion of a guidewire configured according to still another example embodiment.
Figure 6:
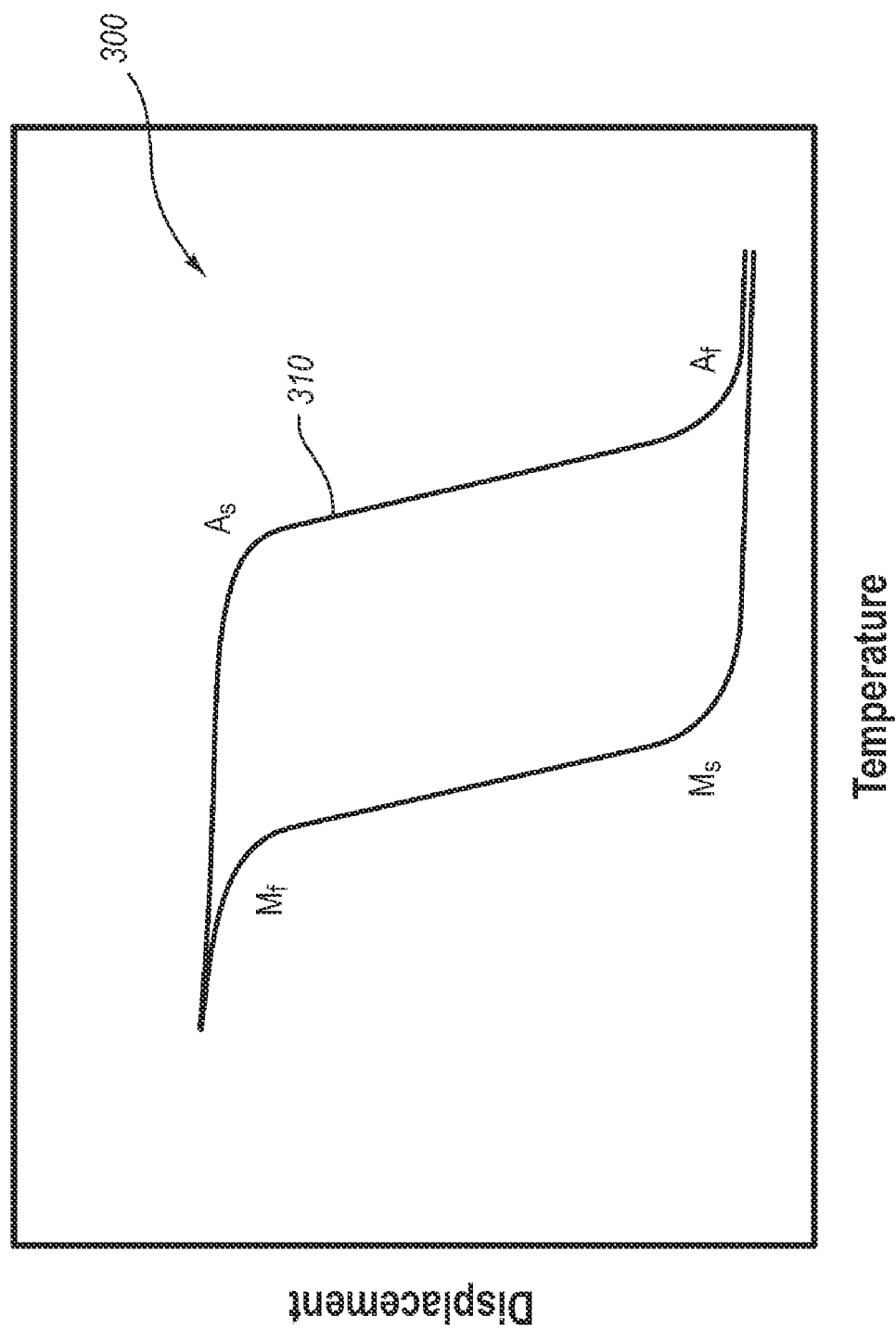
FIG. 6 is a graph showing a typical transition hysteresis curve of nitinol material.

The shaped portion 30 represents only one example of a variety of shapes and deflections that can be formed on a nitinol guidewire. FIGS. 3-5 depict various examples of this principle. Specifically, FIG. 3 shows a proximal shaped portion 130 on a guidewire 10 that is bent with respect to the longitudinal axis 32 of the undeflected portion of the guidewire body 12. The shaped portion 130 is deflected so as to define an angle 0 with the axis 32. FIG. 4 shows a proximal shaped portion 230 that defines a right angle 0 with the axis 32 of the guidewire body 12. FIG. 5 depicts yet another example of a deflection, wherein a portion of the guidewire 10 intermediate the guidewire proximal end 14 and distal end 16 is geometrically shaped to resemble a plateau, thus defining a shaped intermediate portion 330. It is therefore appreciated that the shaped portion can be positioned proximate the proximal guidewire end, or in some other intermediate location along the guidewire. It is further appreciated that the shaped portion can be shaped any one of a variety of ways, such as hook-shaped, circular, semi-circular, square, or other geometric or angled shapes or portions thereof.

In yet another embodiment, a portion of the guidewire manufactured from nitinol or other suitable shape memory material is subjected to heat treatment (e.g., annealing) without first deflecting the portion. By treating it in this manner at a desired temperature, the guidewire portion loses its superelastic characteristics and becomes malleable. Later, when the clinician advances the guidewire into the patient vasculature, the distal portion of the guidewire retains its kink-resistant qualities while the heat-treated portion is malleable. This allows the clinician to bend the guidewire portion, such as the proximal portion, to form a hook or other angled member to prevent migration of the guidewire 10 into the vasculature of the patient. In one possible implementation, the clinician can advance a needle, or other medical apparatus (e.g., vessel dilator, catheter), over the guidewire before bending the proximal portion of the guidewire. In one example embodiment, a 10 cm proximal portion of a nitinol guidewire having a total length of about 50 cm is heat treated so as to be malleable. The remaining 40 cm of the guidewire is left untreated so as to retain preferred kink-resistant qualities. The lengths of the various portions described above are variable according to need for a particular application.

The proximal portion of the guidewire in this embodiment is subject to heat treatment from about thirty seconds to about fifteen minutes at temperatures ranging from about 200 to about 450 degrees Celsius. The guidewire can be heat treated in a conventional oven, an IR oven, by laser, or by any other suitable method. In one aspect, following heat treatment, the guidewire is subjected to a water bath. Note that the temperature and time parameters specified above can vary according to a particular application.

Figure 7:
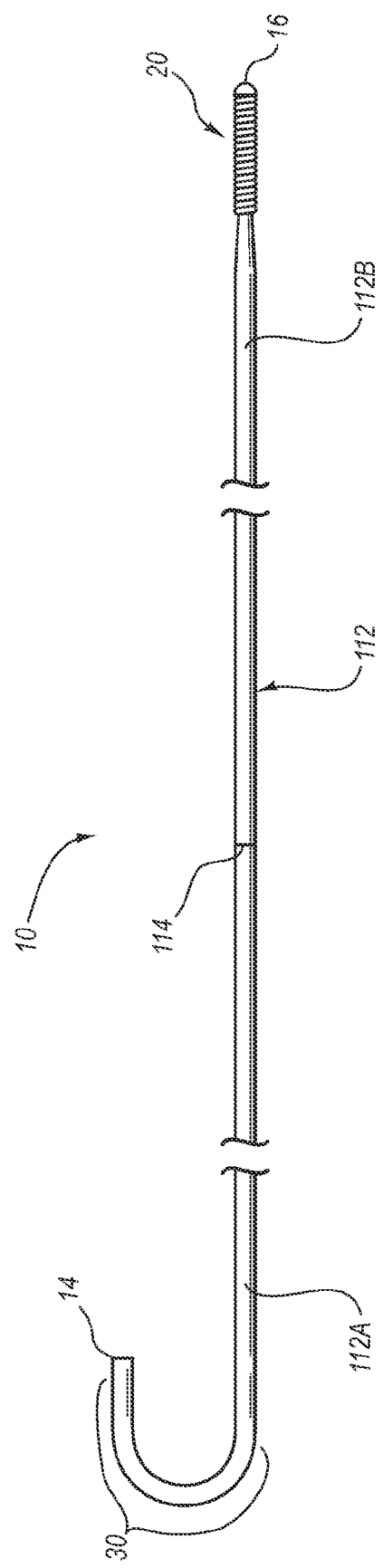
FIG. 7 is a side view of a guidewire configured according to an example embodiment of the present invention.

In another example embodiment, the guidewire can be composed of distinct materials according to guidewire region. This is shown in FIG. 7, wherein the guidewire 10 includes a body 112. The guidewire body 112 includes a proximal segment 112A and a distal segment 112B. The proximal segment 112A, representing a portion of the guidewire body 112 extending from the proximal end 14 and including the shaped portion 30, includes stainless steel, thus giving the proximal portion bendability in order to form the shaped portion.

In contrast, the distal segment 112B extending from the distal end 16, includes nitinol, which gives the distal segment preferred kink-resistant qualities. The proximal and distal segments 112A and 112B can be joined by any suitable process, including bonding, welding, and the like. The relative portion of the guidewire 10 that is defined by the proximal and distal segments 112A and 112B can vary according to the particular application. Further, note that other materials in addition or alternative to stainless steel and nitinol can be included in the respective guidewire segments.

Note that, while the discussion above has focused on guidewires, in other embodiments the principles of the present invention can be applied to other medical apparatus, including for example a stiffening member for use with intravenous catheters. Also, the length of the shaped guidewire portion can vary according to the particular needs of an application.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A guidewire system, comprising:
    a shaped guidewire, comprising:
        an elongate body with a proximal end and a distal end defining a longitudinal axis; and
        a shaped portion made from a shape memory material, the shaped portion having a first configuration, deflected from the longitudinal axis, and designed to be malleable from the first configuration to a second deflected configuration, the shaped portion having a diameter the same as a diameter of the elongate body; and
    an apparatus for positioning at an incision site on a corpus of a patient, the apparatus having a proximal end and a distal end, the apparatus interacting with the shaped portion of the shaped guidewire to prevent the shaped portion from advancing distally of the proximal end of the apparatus.

2. The guidewire system according to claim 1, wherein the shape memory material is a shape memory alloy.

3. The guidewire system according to claim 2, wherein the shape memory alloy includes nickel and titanium.

4. The guidewire system according to claim 3, wherein the shape memory alloy includes nitinol.

5. The guidewire system according to claim 1, wherein the shaped portion is deflected at a 90 degree with respect to the longitudinal axis in the first configuration.

6. The guidewire system according to claim 1, wherein the shaped portion defines a semi-circular shape.

7. A shaped guidewire system, comprising:
    an apparatus having a proximal end and a distal end; and
    a shaped guidewire having a proximal end and a distal end, the shaped guidewire including an elongate body and a shaped portion, the shaped portion composed of a shape memory material and configured to be malleable from a first configuration to a second configuration, the shaped portion having a diameter the same as a diameter of the elongate body, the shaped portion located adjacent the proximal end of the elongate body, the first configuration being deflected from a longitudinal axis defined by the elongate body and shaped to interact with the proximal end of the apparatus and to remain proximal of the proximal end of the apparatus.

* * * * *